United States Patent [19]

Murase et al.

[11] Patent Number: 4,883,947

[45] Date of Patent: Nov. 28, 1989

[54] RESISTANCE CERAMIC HEATER WITH MUTUALLY CONNECTED HEAT-GENERATING CONDUCTORS, AND ELECTROCHEMICAL ELEMENT OR OXYGEN ANALYZER USING SUCH CERAMIC HEATER

[75] Inventors: Takao Murase, Kohnan; Tsunenori Yoshimura, Nagoya, both of Japan

[73] Assignee: NGK Insulators, Ltd., Nagoya, Japan

[21] Appl. No.: 319,159

[22] Filed: Mar. 6, 1989

[30] Foreign Application Priority Data

Mar. 9, 1988 [JP] Japan .................... 63-55471

[51] Int. Cl.⁴ .......................... H05B 3/6; H01C 7/00
[52] U.S. Cl. ................................ 219/553; 219/538; 219/541; 219/548; 73/23; 73/27 R; 324/71.5; 338/34
[58] Field of Search .............. 219/538, 541, 543, 548, 219/553; 338/34, 306, 307; 324/71.5; 73/23, 26, 27 R

[56] References Cited

U.S. PATENT DOCUMENTS

| 4,453,397 | 6/1984 | Ohta | 338/34 |
| 4,697,165 | 9/1987 | Ishiguro | 338/34 |
| 4,733,056 | 3/1988 | Kojima | 219/543 |

Primary Examiner—A. D. Pellinen
Assistant Examiner—Leon K. Fuller
Attorney, Agent, or Firm—Arnold, White & Durkee

[57] ABSTRACT

A resistance ceramic heater including a ceramic substrate, and a heating element which has a resistance heat-generating portion, and electrical leads connected to the heat-generating portion for energizing the heat-generating portion to generate heat. The heat-generating portion consists of a plurality of electrically resistive heat-generating conductors formed in parallel connection with each other and in series connection to the electrical leads, and a plurality of connecting conductors which connects the heat-generating conductors, at a plurality of connection points on each of the heat-generating conductors. The connection points are spaced apart from each other along the length of each heat-generating conductor. An electrochemical element and an oxygen analyzer or sensor which uses the ceramic heater are also disclosed.

12 Claims, 6 Drawing Sheets

RESISTANCE CERAMIC HEATER WITH MUTUALLY CONNECTED HEAT-GENERATING CONDUCTORS, AND ELECTROCHEMICAL ELEMENT OR OXYGEN ANALYZER USING SUCH CERAMIC HEATER

BACKGROUND OF THE INVENTION

1. Field of the Invention

The present invention relates in general to a resistance ceramic heater, an electrochemical element incorporating such a ceramic heater, and an oxygen alanyzing device using such an electrochemical element, and more particularly to a resistance ceramic heater which has improved durability or prolonged life expectancy.

2. Discussion of the Prior Art

A resistance ceramic heater is known according to Laid-Open Publications Nos. 61-109289 (published in 1986), 61-138487 (published in 1986) and 60-212986 (published in 1985) of unexamined Japanese Patent Applications. In the ceramic heater disclosed in these publications, a resistance heating element consisting of an electrically resistive heat-generating conductor, and electrical leads for supply power to the heating element are formed in desired patterns, integrally on a surface of a ceramic substrate. The heating element is generally formed on the ceramic substrate, for example, by screen printing of an electrically conductive material (metal) such as tungsten or platinum. The electrically resistive heat-generating conductor is energized with an electric current supplied thereto from an external power source through the electrical leads, to produce heat based on the electrical resistance of the heat-generating conductor, for heating a desired article or member.

The resistance heating element formed in a suitable pattern may have some defects or flaws at its local portions, for some reason or other in the process of manufacture as by screen printing technique. For example, some portions of the heating element may have an extremely small thickness due to inadequate printing condition, or an abnormally high electrical resistance value due to inclusion of a foreign substance in the material. When the heating element (heat-generating conductor) is energized, a voltage across a defective portion of the element is abnormally or extremely raised, whereby the electrically conductive metal at the defective portion is overheated, sintered or cracked, and may consequently be electrically disconnected. Thus, the defects of the heating element lead to a considerably shortened life expectancy or extremely lowered durability of the ceramic heater.

SUMMARY OF THE INVENTION

It is therefore a first object of the present invention to provide a resistance ceramic heater which has a heating element integrally formed on a ceramic substrate and which is improved in durability and operating reliability.

A second object of the present invention is to provide such a resistance ceramic heater which has prolonged life expectancy even if the electrically resistive heat-generating conductor of the heating element has a defect or an electrically disconnected portion.

It is a third object of the present invention to provide a highly durable and reliable electrochemical element incorporating such a resistance ceramic heater, or a highly durable and reliable oxygen analyzing or sensing device which uses such an electrochemical element.

The first and second objects may be attained according to one aspect of the present invention, which provides a resistance ceramic heater comprising: a ceramic substrate; and a heating element including a resistance heat-generating portion, and electrical leads connected to the heat-generating portion for energizing the heat-generating portion to generate heat. The heat-generating portion consists of a plurality of electrically resistive heat-generating conductors formed in parallel connection with each other and in series connection to the electrical leads, and a plurality of connecting conductors which connects the plurality of heat-generating conductors, at a plurality of connection points on each of the plurality of heat-generating conductors. The connecting points are spaced apart from each other along a length of each heat-generating conductor.

In the resistance ceramic heater of the present invention constructed as described above, the plurality of heat-generating conductors and the plurality of connecting conductors connecting the heat-generating conductors at the plurality of connection points cooperate with each other to form a network of conductors. A defect which may exist at a local portion of the network will not cause the defective portion to be overheated and electrically disconnected due to an abnormally elevated voltage across the defective portion. Even if the defective portion is disconnected, the network of conductors of the heat-generating portion as a whole is able to generate heat, and is not overheated, though the defective portion per se fails to generate heat. Thus, the instant resistance ceramic heater has significantly improved life expectancy or durability and operating reliability.

The resistance heat-generating portion of the instant ceramic heater arranged according to the principle of the invention assures even distribution of heat over the entire area covered by the network of conductors, and therefore permits even distribution of heating temperature, improved heating efficiency, and increased resistance to thermal stresses.

In the instant ceramic heater, the surface layer of the ceramic substrate which contacts the heat-generating portion of the heating element is preferably formed of an electrically insulating ceramic material. Further, it is desirable that the electrically insulating layer of the ceramic substrate cooperate with another electrically insulating layer to sandwich the heat-generating portion of the heating element. In other words, the heat-generating portion is desirably embedded in a mass of an electrically insulating material, which includes the surface layer of the ceramic substrate.

In another advantages form of the invention, at least the heat-generating portion of the heating element is co-fired with the ceramic substrate, so that the durability of the heat-generating portion at an elevated operating temperature is further improved.

The heat-generating portion of the heating element is generally formed of a cermet which consists of a ceramic material, and an electrically conductive metallic material which contains a noble metal as a major component. Preferably, platinum is used as the major component of the electrically conductive metallic material of the cermet. For improved adhesion of the heating element to the ceramic substrate, it is desirable that the ceramic material of the cermet be substantially the same as a ceramic material of the ceramic substrate.

The positions of the connection points of the heat-generating conductors are preferably determined such that the connecting conductors of the heat-generating portion have a volume resistivity value not higher than a half of that of the heat-generating conductors. In this case, the electrical resistance values of the connecting conductors do not exceed a half of the electrical resistance values of the divisions or portions of the heat-generating conductors which are defined by the adjacent connection points.

The plurality of heat-generating conductors of the heat-generating portion of the heating element may consist of two parallel heat-generating conductors which cooperate with the connecting conductors to form a ladder-like arrangement. Alternatively, the three or more heat-generating conductors may cooperate with the connecting conductors to form a grid or lattice.

The resistance ceramic heater according to the above aspect of the invention may be suitably used for various purposes, for examples, as a glow plug, a burner ignitor, and heaters for various gas sensors or analyzers. In particular, the instant ceramic heater is advantageously utilized as a heater for heating an electrochemical element of gas sensors such as an oxygen sensor adapted to determine or measure the oxygen concentration of exhaust emissions of internal combustion engines for automotive vehicles. Such an electrochemical element has at least one electrochemical cell each of which includes a solid electrolyte body, and at least one pair of electrodes formed on the solid electrolyte body. The instant ceramic heater is positioned in the electrochemical element so that the electrochemical cell or cells is/are effectively heated by the ceramic heater.

That is, the third object of the invention may be accomplished, according to another aspect of the invention, which provides an electrochemical element comprising at least one electrochemical cell including a solid electrolyte body, and at least one pair of electrodes formed on the solid electrolyte body, and further comprising a resistance ceramic heater which includes a ceramic substrate, and a heating element having a resistance heat-generating portion, and electrical leads connected to the heat-generating portion for energizing the heat-generating portion to generate heat. The heat-generating portion consists of a plurality of electrically resisitive heat-generating conductors formed in parallel connection with each other and in series connection to the electrical leads, and a plurality of connecting conductors which connects the plurality of heat-generating conductors, at a plurality of connection points on each of the plurality of heat-generating conductors. The connecting points are spaced apart from each other along the length of each heat-generating conductor.

The electrochemical element may be suitably used for an oxygen analyzing device. In other words, the ceramic heater of the invention may be used for such an oxygen analyzing device.

That is, the third object may also be accomplished according to a further aspect of the present invention, which provides an oxygen analyzing device comprising at least one electrochemical cell including an oxygen-ion conductive solid electrolyte body, and at least one pair of electrodes formed on the solid electrolyte body, and further comprising a resistance ceramic heater which includes a ceramic substrate, and a heating element having a resistance heat-generating portion, and electrical leads connected to the heat-generating portion for energizing the heat-generating portion to generate heat. The heat-generating portion consists of a plurality of electrically resistive heat-generating conductors formed in parallel connection with each other and in series connection to the electrical leads, and a plurality of connecting conductors which connects the plurality of heat-generating conductors, at a plurality of connection points on each of the plurality of heat-generating conductors. The connecting points are spaced apart from each other along a length of the each heat-generating conductor.

By using the ceramic heater as described above, the electrochemical element or the oxygen analyzing or sensing device may be operated at an optimum temperature for accurate and reliable operation, for a comparatively long period of service life.

BRIEF DESCRIPTION OF THE DRAWINGS

The above and other objects, features and advantages of the present invention will be better understood by reading the following detailed description of presently preferred embodiments, when taken in connection with the accompanying drawings, in which.

DETAILED DESCRIPTION OF THE PREFERRED EMBODIMENTS

To further clarify the concept of the present invention, there will be described some forms of the ceramic resistance heaters of the invention, and some arrangements of the electrochemical element incorporating such a ceramic resistance heater of the invention, by reference to the accompanying drawings.

Figure 1:
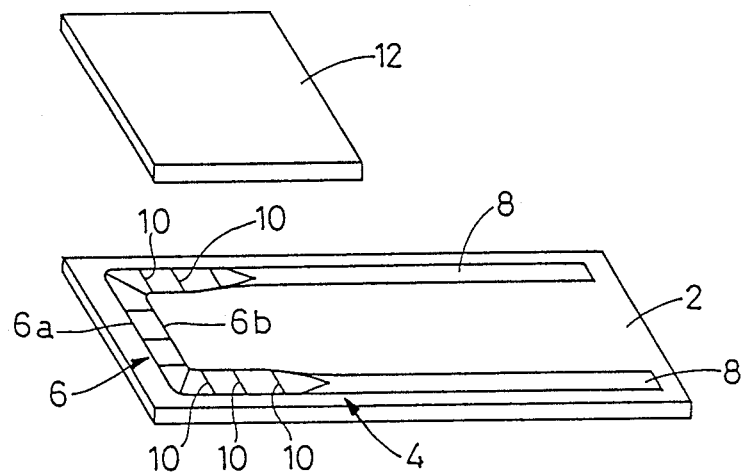
FIG. 1 is an exploded perspective view of a simplest form of a ceramic resistance heater according to one embodiment of the invention.

Referring first to FIG. 1, reference numeral 2 designates a ceramic substrate formed of a suitable ceramic material. On one of the opposite major surfaces of the ceramic substrate 2, there is integrally formed a heating element 4. This heating element 4 consists of a resistance heat-generating portion 6 energized to generate heat, and two electrical leads 8, 8 for connecting the heat-generating portion 6 to an external power source (not shown), for supplying power to the heat-generating portion 6.

The resistance heat-generating portion 6 of the heating element 4 includes two heat-generating conductors 6$a$, 6$b$ formed in suitable patterns so as to extend in parallel with each other. These two heat-generating conductors 6$a$, 6$b$ are connected in series at their opposite ends to the electrical leads 8, 8. The two heat-generating conductors 6$a$, 6$b$ are further connected to each other by a plurality of connecting conductors 10, at the corresponding points at which the potentials of the two conductors 6$a$, 6$b$ are substantially equal to each other. Thus, the resistance heat-generating portion 6 as a whole takes the form of a ladder, as indicated in FIG. 1., wherein the two heat-generating conductors 6a, 6b are disposed in parallel connection with each other, with respect to the electrical leads 8.

To form the heat-generating portion 6 and the electrical leads 8 of the heating element 4 on the ceramic substrate 2, selected materials are applied to the appropriate major surface of the ceramic substrate 2, by a suitable known technique such as sreen printing, in desired patterns, and the applied materials are fired or baked into the heating element 4. For improved durability of the heater, the electrical leads 8 as well as the resistance heat-generating portion 6 are preferably co-fired with the ceramic substrate 2. In this case, the heat-generating element 6 and the electrical leads 8 are both formed of a cermet or respective cermets each including a ceramic material and an electrically conductive material. For improved adhesion of the heating element 4 to the ceramic substrate 2, the cermet used for the element 4 usually includes a ceramic material similar to the material of the ceramic substrate 2. The electrically conductive material is generally selected from among noble metals, and preferably from the platinum-group, particularly, platinum, rhodium, palladium, osmium and iridium. More preferably, platinum is used as a major component of the electrically conductive material contained in the cermet.

It is noted, however, that the composition for the electrical leads 8 need not be the same as that for the heat-generating portion 6, but may include a non-noble or base metal as a major component or may consist of a cermet inlcuding a base metal and a ceramic material. For example, the base metal may be selected from among niobium, molybdenum, tantalum, tungsten, other metals having a relatively high melting point, aluminum, titanium, chromium, manganese, iron, cobalt, nickel, copper, and similar metals, and alloys of the metals indicated above.

The ceramic substrate 2 carrying the heating element 4 integrally formed thereon are formed of a ceramic material whose major component consists, for example, of zirconia, alumina, mullite, cordierite, forsterite, beryllia or silicon nitride, or a mixture thereof. Further, the heating element 4 may be formed on a ceramic layer which is formed of the above ceramic material on a metallic layer or plate. While the ceramic substrate 2 is desirably formed to a sheet-like or planar shape, for easy manufacture, the substrate may have other shapes, such as a tube or cylinder.

The heat-generating portion 6 of the heating element 4 formed on the ceramic substrate 2 is covered and protected by a protective layer 12 made of alumina or other suitable material, whereby a resistance ceramic heater having a laminar structure is formed. The protective layer 12 may be either a dense gas-tight layer or a porous layer. Where the protective layer 12 is a dense gas-tight layer, the protective layer 12 effectively prevents the volatilization of the conductive metal of the heat-generating portion 6 at an elevated operating temperature, and protects the heat-generating portion 6 from the surrounding or ambient atmosphere. Where the protective layer 12 is a porous layer, thermal stresses may be effectively absorbed or mitigated by the porous protective layer 12. In the present embodiment wherein the heat-generating portion 6 is sandwiched between the alumina ceramic substrate 2 and the alumina protective layer 12, the heat-generating portion 6 is suitably electrically insulated.

Figure 2:
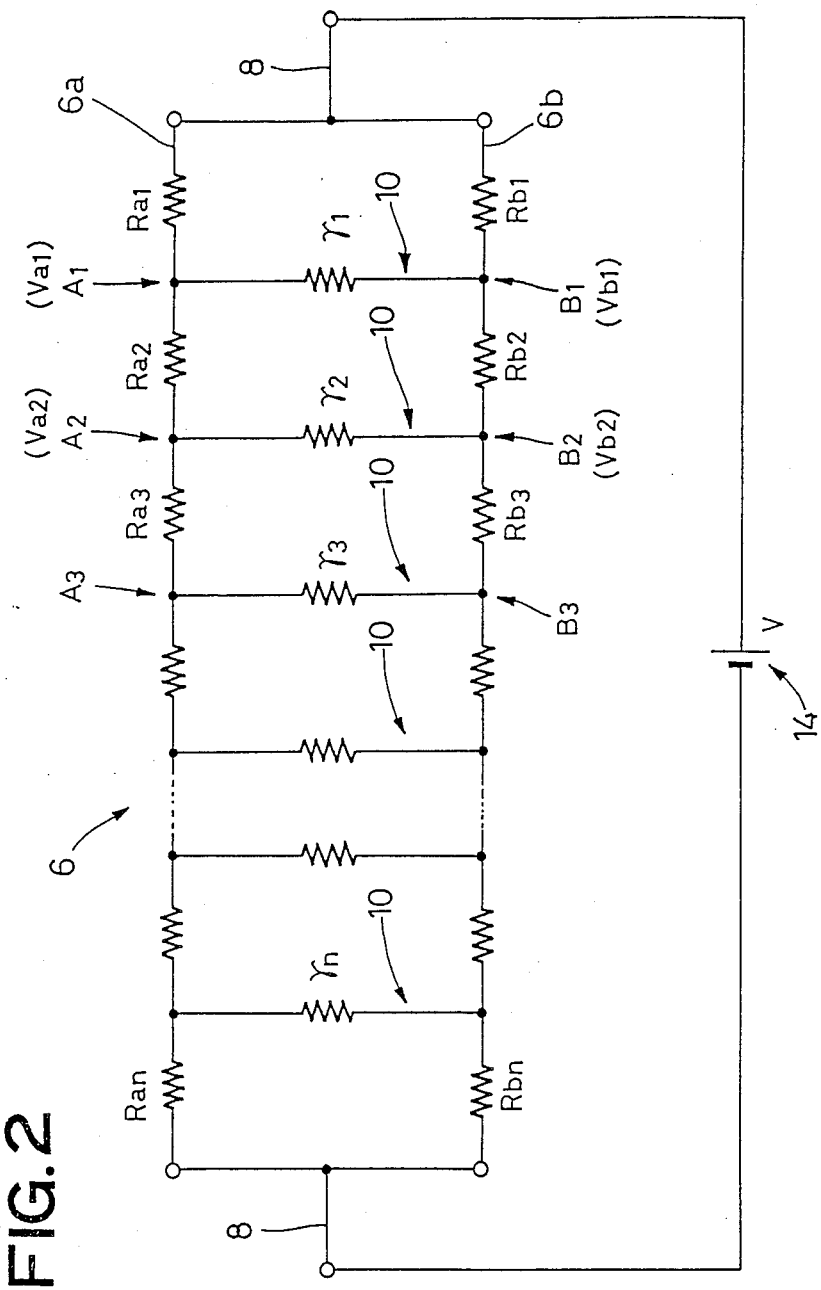
FIG. 2 is a diagram showing an electric circuit equivalent to a heating element of the ceramic resistance heater of FIG. 1.

Referring to FIG. 2, there is illustrated an electric circuit equivalent to the heating element 4 of the instant resistance ceramic heater. In the figure, reference numeral 14 denotes a DC power source to which the electrical leads 8, 8 are electrically connected, to supply a DC current to the heat-generating conductors 6a, 6b of the resistance heat-generating portion 6. The two conductors 6a, 6b are connected to each other at points Ai (i=1, 2, 3, ... i) and Bi (i=1, 2, 3, ... i) by the respective connecting conductors 10. The divisions of the heat-generating conductors 6a, 6b which are defined by the connection points Ai, Bi have respective electrical resistance values Ran (n=1, 2, 3, ... n) and Rbn (n=1, 2, 3, ... n). On the other hand, the connecting conductors 10 have respective electrical resistance values rn.

In the heating element 4 formed in the form of a ladder consisting of the heat-generating conductors 6a, 6b and the connecting conductors 10, a voltage applied to the heat-generating portion 6 will not be concentrated on a defective portion of the heat-generating conductors 6a, 6b which may occur during manufacture for some reason or other.

For instance, where the division of the conductor 6a which should have the resistance value Ra2 is defective and has an extremely increased resistance value Ra2', the current applied to the conductor 6a flows to the other conductor 6b, via the connection point A1 and through the connecting conductor 10 having the resistance value r1, and then flows back to the conductor 6a, via the connection points B1 and B2 and through the connecting conductor 10 having the resistance value r2. Thus, the electric current flowing through the division having the abnormally increased resistance value Ra2' merges at the connection point A2, with the electric current flowing from the connection point B2, and the sum of the currents flows through the division having the resistance value Ra3. Consequently, the voltage at the defective division having the increased resistance value Ra2' will not be abnormally elevated.

Accordingly, such a defective division (indicated at Ra2 in FIG. 2, in the above example) of the heat-generating conductors 6a, 6b is less likely to be heated to a high temperature, and is consequently protected from breakage or electrical disconnection. Even if the conductors 6a, 6b were disconnected at the defective division, the heating element 4 will not be overheated, though the disconnected division fails to generate heat. In the event of disconnection of the division Ra2 of the conductor 6a as indicated above, for example, the current flows from the connection point A1 of the conductor 6a to the connection point B1 of the conductor 6b, and then flows back to the connection point A2 through the division Rb2, connection point B2 and the corresponding connecting conductor 10. Thereafter, the current flows from the division Ra3 up to the division Ran of the conductor 6a. Hence, the heating element 4 having the thus constructed heat-generating portion 6 will not be overheated even if a defect exists in the heat-generating portion 6, and thus enables the resistance ceramic heater to have extremely long life expectancy and significantly improved operating reliability.

Further, the electrical connection of the two heat-generating conductors 6a, 6b by the plurality of connecting conductors 10 permits the two conductors 6a, 6b to have the same potentials at the corresponding connection points Ai and Bi, whereby the amount of power consumption and the heating temperature of the heat-generating portion 6 is averaged over the entire area of the heating pattern. Accordingly, the instant ceramic heater assures high heating efficiency, even temperature distribution, and improved resistance to thermal stresses.

The connection points Ai and Bi at which the two heat-generating conductors 6a, 6b are connected by the connecting conductors 10 are preferably determined so that the voltage across each point Ai is substantially equal to the voltage across the corresponding point Bi. For example, the positions of the connection points A1 and B1 connected by one conductor 10, and the positions of the connection points A2 and B2 connected by the next conductor 10, are determined so that a voltage Va1 across the point A1 is substantially equal to a voltage Vb1 across the corresponding point B1, while a voltage Va2 across the next point A2 is substantially equal to a voltage Vb2 across the corresponding point B2. However, the connection points Ai and Bi may be determined such that a difference $\Delta Vi$ between the voltages Vai and Vbi is not higher than 20% of a voltage V of the heater power source 14, for smooth flows of the current through the heating element 4.

While it is ideal that the electrical resistance values rn of the connecting conductors 10 are zero (0), it is impossible to use the conductors 10 whose resistance values are zero. Practically, the resistance values rn should not exceed a half of the resistance values Ran of the conductor 6a (rn$\leq$Ran/2, where Ran$\leq$Rbn). To this end, the connecting conductors 10 are formed by screen printing or other method, so that their volume resistivity is not higher than a half of that of the heat-generating conductors 6a, 6b. As described above, the connecting conductors 10 are preferably formed of a cermet similar to a cermet used for the heat-generating conductors 6a, 6b. In this case, the electrical resistance values rn of the conductors 10 may be lowered by increasing the content of the electrically conductive metal of the cermet.

The heat-generating portion 6 of the heating element 4 of the resistance ceramic heater according to the present invention may have different patterns or forms other than that shown in FIG. 1. For example, the heat-generating portion 6 may have modified patterns as illustrated in FIGS. 3(a) through 3(e).

Figure 3A:
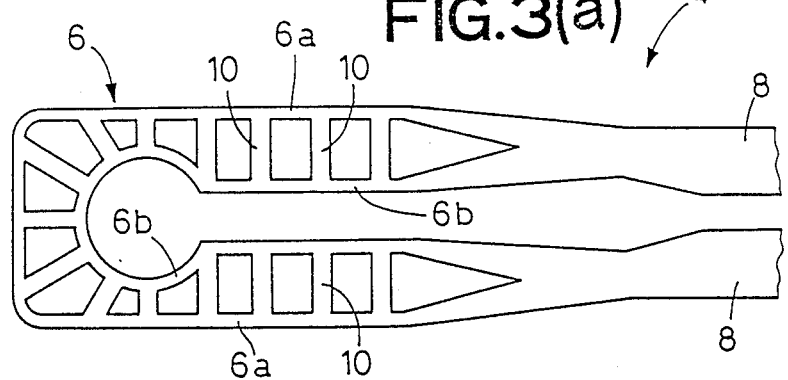
FIGS. 3($a$) through 3($e$) are fragmentary schematic plan views showing different forms of resistance heat-generating portions of ceramic heaters according to different embodiments of the invention.
Figure 3B:
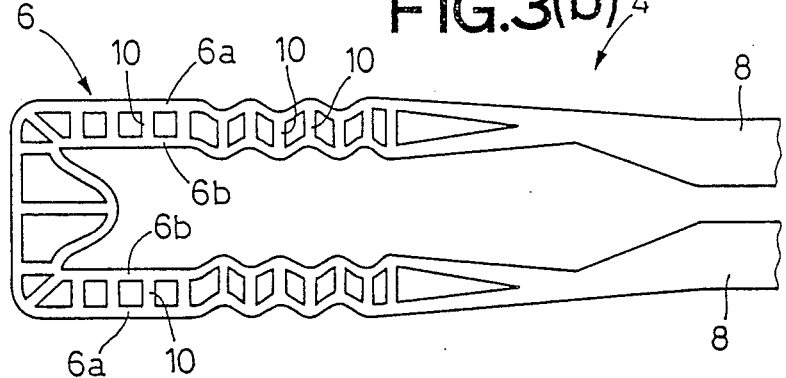

The patterns shown in FIGS. 3(a) and 3(b) are variants of the ladder-like pattern of FIG. 1, wherein two heat-generating conductors 6a, 6b formed in parallel connection to the electrical leads 8 are connected to each other by the connecting conductors 10 at a plurality of connection points, which are spaced apart from each other along the lengths of the conductors 6a, 6b.

Figure 3C:
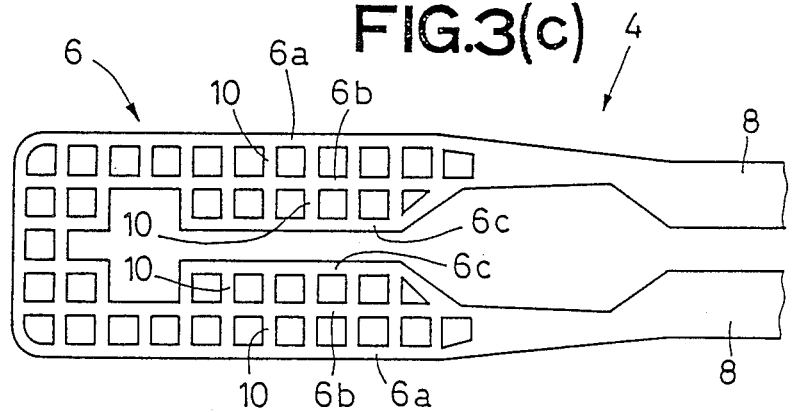
Figure 3D:
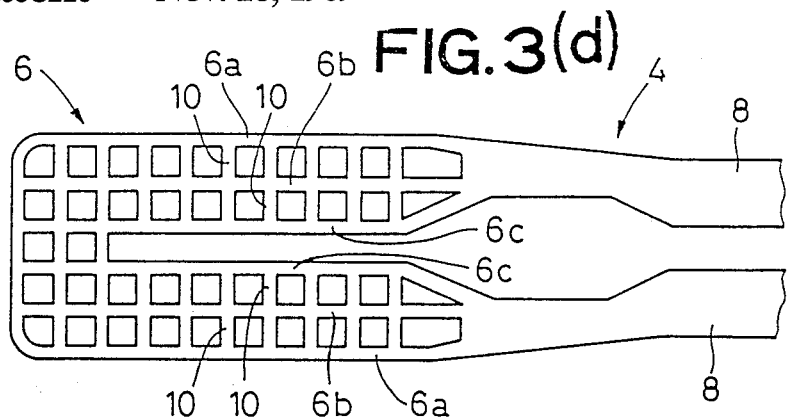

The heat-generating portions 6 illustrated in FIGS. 3(c) and 3(d) have three heat-generating conductors 6a, 6b and 6c which are connected to each other by the connecting conductors 10, at a plurality of connection points arranged along the lengths of the conductors 6a–6c, such that the three heat-generating conductors 6a, 6b, 6c and the connecting conductors 10 cooperate with each other to define a grid or lattice. In the embodiment of FIG. 3(c), the conductor 6c is disconnected at several positions along the length of the heat-generating portion 6, and merges with the adjacent conductor 6b at those positions.

Figure 3E:
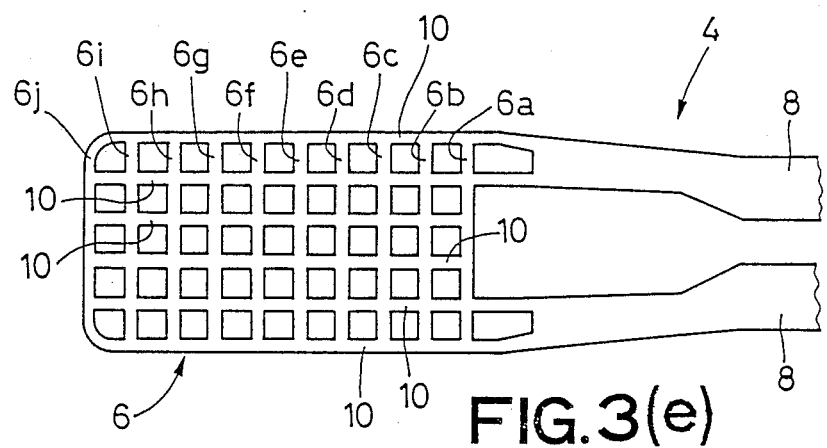

In the embodiment of FIG. 3(e), the heat-generating portion 6 consists of a relatively large number of heat-generating conductors 6a, 6b, ... 6j which extend perpendicular to the lengths of the electrical leads 8, and a plurality of connecting conductors 10 perpendicular to the conductors 6a–6j, whereby the heat-generating portion 6 takes the form of a grid pattern.

On the other hand, a heating element of a conventional resistance ceramic heater has a heat-generating portion 6 which consists of a single serpentine or meandering heat-generating conductor connected at its opposite ends to the electrical leads 8, 8. In this conventional arrangement, a defective portion of the single heat-generating conductor 6 may cause an abnormally elevated voltage at that local defective portion, and resulting disconnection of the heating element, which results in reduced life expectancy of the ceramic heater.

The advantages of the resistance ceramic heater according to the present invention will become more apparent from the following description of Examples:

EXAMPLES

Initially, an alumina paste was applied by printing to one surface of each of a total of sixty zirconia green sheets, so that an unfired alumina layer was formed on each green sheet. After the alumina layers were dried, a platinum paste was applied by printing to the alumina layers on the zirconia green sheets, to form heating elements having three different patterns [a], [b] and [c] of a heat-generating portion, on the respective sets of zirconia green sheets, each set consisting of twenty sheets. Another unfired alumina layer and another zirconia green sheet were formed so as to cover the heating element. The thus obtained laminar structures each having the heating element sandwiched between the two zirconia green sheets were fired into the corresponding ceramic heaters, which are classified into three groups, depending upon the patterns of the heat-generating portion.

Figure 4:
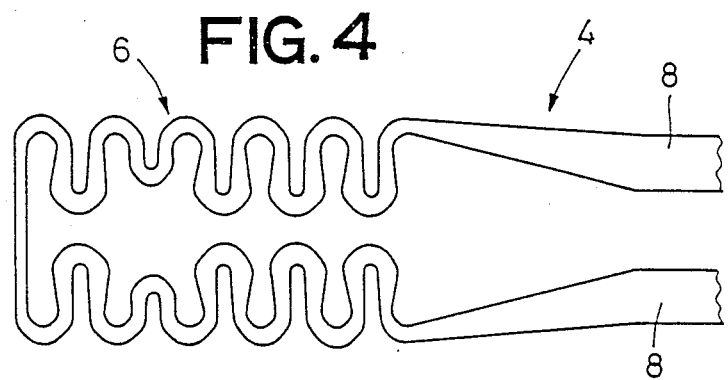
FIG. 4 is a fragmentary schematic plan view showing a resistance heat-generating portion of a known heating element.

The heat-generating pattern [a], which is shown in FIG. 4, was used for a group of the twenty comparative ceramic heaters, which will be referred to as Comparative Example [A]. The pattern [b] has the heat-generating conductors 6a and 6b of FIG. 3(a) but does not have the connecting conductors 10. This pattern [b] was used for another group of the twenty comparative ceramic heaters, which will be referred to as Comparative Example [B]. The pattern [c], which is shown in FIG. 3(a), was used for a group of the twenty ceramic heaters according to the present invention, which will be referred to as Inventive Example [C].

The heating elements of all the ceramic heaters (Comparative Examples [A] and [B], and Inventive Example [C]) have an electrical resistance value of 5.5–6.5$\Omega$. The platinum paste used for the heat-generating conductors 6, 6a, 6b of the heat-generating patterns [a] and [b] of Comparative Examples [A] and [B] has a platinum (Pt) content of 60% by volume. For the heat-generating pattern [c] of Inventive Example [C], the platinum paste has a Pt content of 60% by volume for the heat-generating conductors, and 90% by volume for the connecting conductors 10. The remaining content of the platinum pastes consists of a ceramic material principally consisting of alumina.

The ceramic heaters of Comparative Examples [A] and [B] and Inventive Example [C] were subjected to a continuous energization test for 5000 hours at a room temperature in the atmosphere, with a DC voltage of 16V applied to the heating elements. Further, the ceramic heaters were subjected to a discontinuous energization test at $-40°$ C., wherein 50000 on-off cycles were effected, each with the heating elements energized with DC 16V for five minutes and deenergized for five minutes.

The continuous energization test revealed that the heating elements were electrically disconnected on the two ceramic heaters of Comparative Example [A] and the three ceramic heaters of Comparative Example [B]. However, none of the twenty ceramic heaters of Inventive Example [C] suffered from electrical disconnection of the heating elements. The discontinuous energization test revealed electrical disconnection of the heating elements on the two ceramic heaters for both of Comparative Examples [A] and [B], while no electrical disconnection was found for Inventive Example [C].

Figure 5:
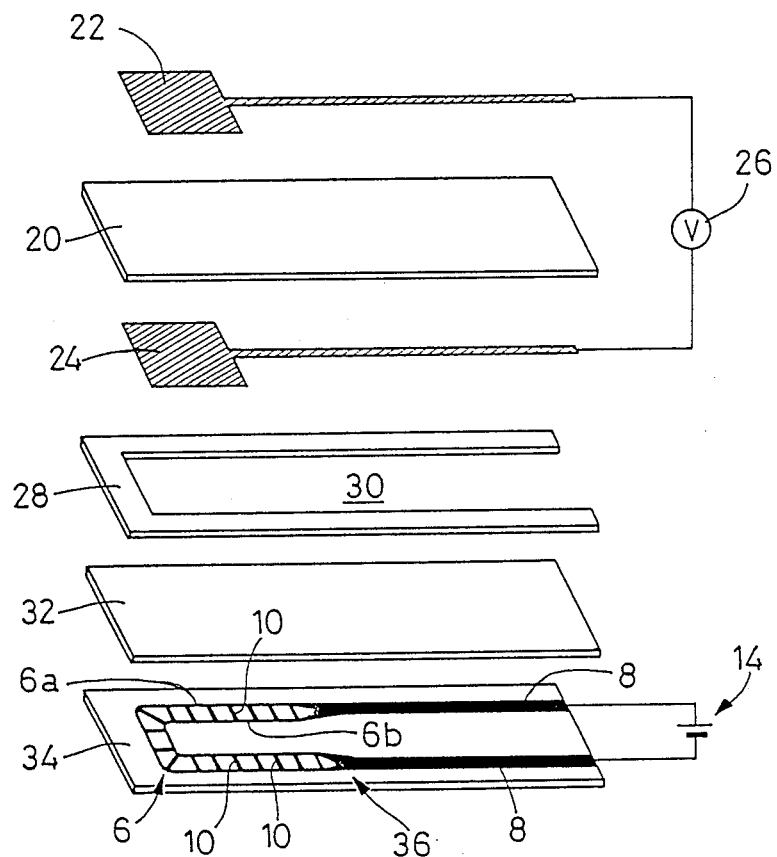
FIGS. 5 and 6 are exploded perspective views illustrating examples of an electrochemical element incorporating a ceramic heater of the present invention.

While the resistance ceramic heater according to the present invention may be used for various purposes, an example of application of the instant ceramic heater is depicted in FIG. 5, which shows a simplest form of an electrochemical oxygen sensing element which incorporates the ceramic heater of the invention. For efficient heating of the electrochemical oxygen sensing element or cell, the sensing element and the ceramic heater are co-fired into a heater-built-in sensing element in which the ceramic heater is formed as an integral part of the sensing element.

Described in detail by reference to FIG. 5, the electrochemical cell forming the oxygen sensing element includes a planar solid electrolyte body 20 made of an oxygen-ion conductive ceramic material such as zirconia, as well known in the art. The solid electrolyte body 20 carries a pair of electrodes, i.e., a measuring electrode 22 and a reference electrode 24 formed on its opposite major surfaces. The electrodes 22, 24 are electrically connected through suitable leads to an external detecting device, e.g., a potentiometer as indicated at 26 in FIG. 5, so that the oxygen concentration of an atmosphere to which th measuring electrode 22 is exposed is detected by the potentiometer 26, according to the principle of a known oxygen concentration cell. The reference electrode 24 is exposed to a reference gas such as the air existing in a reference gas passage 30 which is defined by the solid electrolyte material 20, a U-shaped spacer member 28 of zirconia or other ceramic material, and an electrically insulating layer 32. The spacer member 28 is interposed between the solid electrolyte body 20 and the electrically insulating layer 32.

The electrically insulating layer 32 consists of a dense layer of zirconia or other ceramic material having a high electrical resistance. This insulating layer 32 constitutes a part of a resistance ceramic heater for heating the electrochemical element or cell (20, 22, 24) via the spacer member 28. The ceramic heater includes a heating element 36 according to the principle of the invention, which is formed between and integrally with the electrically insulating layer 32 and another electrically insulating layer 34 similar to the layer 32. The heating element 36 has the same arrangement or pattern as the heating element 4 shown in FIG. 1. No redundant description of the heating element 36 will be described, with the same reference numerals as used in FIG. 1 being used in FIG. 5 to identify the corresponding parts.

The instant electrochemical element incorporating the ceramic heater whose heating element 36 is less likely to be disconnected can operate at a controlled operating temperature, with high oxygen detecting accuracy, for a prolonged period of time. Further, the arrangement of the heat-generating portion 6 of the heating element 36 assures even distribution of heat over the detecting portion of the electrochemical element, for improved accuracy of measurement of oxygen concentration of the subject measurement gas.

Figure 6:
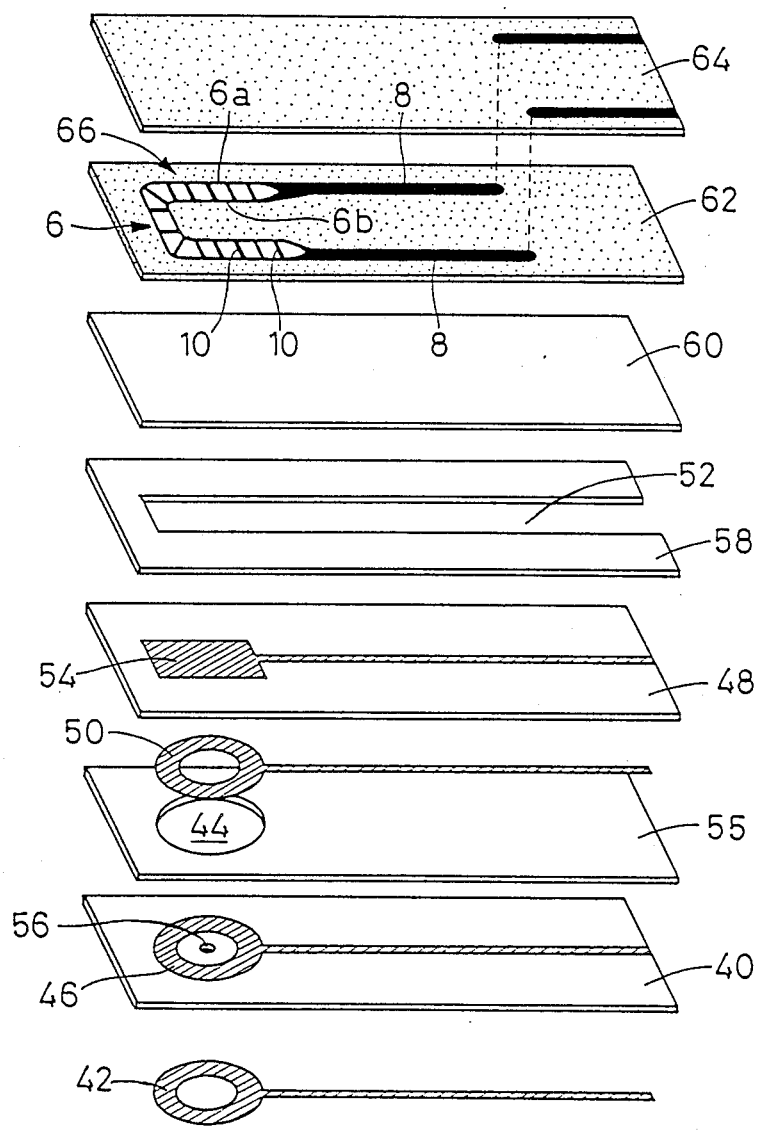

While the electrochemical sensing element of FIG. 5 includes only one electrochemical cell, the ceramic heater of the invention is equally applicable to an electrochemical sensing element which has a plurality of electrochemical cells, as illustrated in FIG. 6, for detecting or measuring the concentration of a desired component of the measurement gas.

Described more specifically, the electrochemical sensing element shown in FIG. 6 uses two electrochemical cells, that is, an electrochemical pumping cell and an electrochemical sensing cell. The pumping cell has a planar solid electrolyte body 40, an annular outer pumping electrode 42 exposed to the external measurement gas, and an annular inner pumping electrode 46 exposed to a circular thin flat space 44. The electrochemical sensing cell has a planar solid electrolyte body 48, an annular measuring electrode 50 exposed to the circular thin flat space 44, and a reference electrode 54 exposed to a reference gas passage 52.

The circular thin flat space 44 is defined such that a round hole formed through a spacer member 55 of zirconia or similar material between the solid electrolyte bodies 40, 48 are closed by these solid electrolyte bodies 40, 48. The thin flat space 44 communicates with the external measurement gas through a gas-inlet aperture 56 formed through the solid electrolyte body 40, such that the aperture 56 is open at a central portion of the thin flat space 44. The external measurement gas is therefore introduced into the circular thin flat space 44 through the gas-inlet aperture 56, and the measurement gas diffuses in the radial direction within the thin flat space 44, under a predetermined diffusion resistance provided by a relatively small thickness of the space 44. The measurement gas therefore contacts the inner pumping electrode 46 and the measuring electrode 50. On the other hand, the reference gas passage 52 to which the reference electrode 54 is exposed is defined such that a rectangular cutout formed in a spacer member 58 of zirconia or similar material is closed by the solid electrolyte body 48 and a covering layer 60 of zirconia or similar material. The passage 52 communicates at its one end with the ambient atmosphere or air.

Where the electrochemical element of FIG. 6 is used for an oxygen sensor, a suitable external detecting device detects an electromotive force which is induced between the measuring and reference electrodes 50, 54 (which cooperate with the solid electrolyte body 48 to constitute an oxygen concentration cell), due to a difference in oxygen concentration between the measurement gas which diffuses in the thin flat space 44, and the reference gas (ambient air) existing in the reference gas passage 52. At the same time, a controlled electric current is applied between the outer and inner pumping electrodes 42, 46 (which cooperate with the solid electrolyte body 40 to constitute another oxygen concentration cell), in order to effect an oxygen pumping operation so that the oxygen concentration of the atmosphere within the thin flat space 44 to which the inner pumping electrode 46 and the measuring electrode 50 are exposed is controlled to a predetermined value. The oxygen concentration of the measurement gas may be determined by measuring the electric current applied to the two pumping electrodes 42, 46.

The electrochemical sensing element having the pumping and sensing cells constructed as described above also incorporates an integrally formed ceramic heater formed on the outer surface of the covering layer 60. The ceramic heater includes two electrically insulating layers 62, 64 made of alumina or similar material, and a heating element 66 sandwiched between the two insulating layers 62, 64. The heating element 66 is similar in arrangement to the heating element 4, 36 shown in FIGS. 1 and 5.

In the embodiment of FIG. 6, the parts of electrical leads 8 of the heating element 66 which are adjacent to the heat-generating portion 6 are formed on the inner insulating layer 62, and the remaining parts of the leads 8 are formed on the outer surface of the outer insulating layer 64. These parts of the leads 8 are connected by conductors disposed in holes formed through the outer insulating layer 64, as indicated by dashed lines in FIG. 6. The electrical leads 8 are connected, at their ends remote from the heat-generating portion 6, to the external detecting device or circuit.

The instant electrochemical sensing element is also efficiently heated by the ceramic heater, for accurate and reliable operation at an optimum temerature for a prolonged period of time.

In the illustrated embodiments, the solid electrolyte bodies are formed of stabilized zirconia ($ZrO_2$). While it is advantageous to use an oxygen-ion conductive solid electrolyte whose major component consists of such zirconia, particularly where the electrochemical sensing element is used for an oxygen concentration detector or oxygen analyzer, the solid electrolyte bodies may be formed of other oxygen-ion conductive solid electrolyte materials, such as $SrCeO_3$, or a solid solution of $Bi_2O_3$ and oxides of rare earth. Where the electrochemical sensing element is used for detecting a component of a measurement gas other than oxygen, the solid electrolyte bodies are formed of a solid electrolyte material which is suitable to that component to be detected.

While the present invention has been described in its presently preferred embodiments in the form of a resistance ceramic heater, an electrochemical element incorporating the ceramic heater, and an electrochemical device such as an oxygen analyzer using such an electrochemical element, it is to be understood that the invention is not limited to the illustrated embodiments, but the principle of the present invention may be practiced, with various changes, modifications and improvements, which may occur to those skilled in the art, without departing from the spirit and scope of the invention defined in the following claims.

What is claimed is:

1. A resistance ceramic heater comprising:
   a ceramic substrate; and
   a heating element including a resistance heat-generating portion, and electrical leads connected to said heat-generating portion for energizing the heat-generating portion to generate heat,
   said heat-generating portion consisting of a plurality of electrically resistive heat-generating conductors formed in parallel connection with each other and in series connection to said electrical leads, and a plurality of connecting conductors which connects said plurality of heat-generating conductors, at a plurality of connection points on each of said plurality of heat-generating conductors, said connecting points being spaced apart from each other along a length of said each heat-generating conductor.

2. A resistance ceramic heater according to claim 1, wherein said ceramic substrate includes an electrically insulating layer which contacts said heat-generating portion of said heating element, said electrically insulating layer being formed of an electrically insulating ceramic material.

3. A resistance ceramic heater according to claim 2, further comprising another electrically insulating layer which is formed of an electrically insulating ceramic material and which cooperates with said electrically insulating layer of said ceramic substrate to provide a ceramic structure in which said heat-generating portion is embedded.

4. A resistance ceramic heater according to claim 1, wherein at least said heat-generating portion of said heating element is co-fired with said ceramic substrate.

5. A resistance ceramic heater according to claim 1, wherein said heat-generating portion of said heating element is formed of a cermet which consists of a ceramic material, and an electrically conductive metallic material which contains a noble metal as a major component.

6. A resistance ceramic heater according to claim 5, wherein said noble metal as the major component of said electrically conductive metallic material of said cermet consists of platinum.

7. A resistance ceramic heater according to claim 5, wherein said ceramic material of said cermet is substantially the same as a ceramic material of said ceramic substrate.

8. A resistance ceramic heater according to claim 1, wherein said connecting conductors of said heat-generating portion have a volume resistivity value which is not higher than a half of that of said heat-generating conductors.

9. A resistance ceramic heater according to claim 1, wherein said plurality of heat-generating conductors of said heat-generating portion of said heating element consist of two parallel heat-generating conductors.

10. A resistance ceramic heater according to claim 1, wherein said plurality of heat-generating conductors and said plurality of connecting conductors of said heat-generating portion of said heating element cooperate with each other to form a grid.

11. An electrochemical element comprising:
    at least one electrochemical cell including a solid electrolyte body, and at least one pair of electrodes formed on said solid electrolyte body; and
    a resistance ceramic heater which includes a ceramic substrate, and a heating element having a resistance heat-generating portion, and electrical leads connected to said heat-generating portion for energizing the heat-generating portion to generate heat,
    said heat-generating portion consisting of a plurality of electrically resistive heat-generating conductors formed in parallel connection with each other and in series connection to said electrical leads, and a plurality of connecting conductors which connects said plurality of heat-generating conductors, at a plurality of connection points on each of said plurality of heat-generating conductors, said connecting points being spaced apart from each other along a length of said each heat-generating conductor.

12. An oxygen analyzing device comprising:

at least one electrochemical cell including an oxygen-ion conductive solid electrolyte body, and at least one pair of electrodes formed on said solid electrolyte body; and a resistance ceramic heater which includes a ceramic substrate, and a heating element having a resistance heat-generating portion, and electrical leads connected to said heat-generating portion for energizing the heat-generating portion to generate heat, said heat-generating portion consisting of a plurality of electrically resistive heat-generating conductors formed in parallel connection with each other and in series connection to said electrical leads, and a plurality of connecting conductors which connects said plurality of heat-generating conductors, at a plurality of connection points on each of said plurality of heat-generating conductors, said connecting points being spaced apart from each other along a length of said each heat-generating conductor.

* * * * *